United States Patent
Nieves-Ramírez

(10) Patent No.: US 7,252,088 B1
(45) Date of Patent: Aug. 7, 2007

(54) METHODS OF POWERING MEDICAL EQUIPMENT FOR THE TREATMENT OF SLEEP APNEA

(76) Inventor: Ismael Nieves-Ramírez, P.O. Box 360537, San Juan, PR (US) 00936-0537

( * ) Notice: Subject to any disclaimer, the term of this patent is extended or adjusted under 35 U.S.C. 154(b) by 0 days.

(21) Appl. No.: 11/358,630

(22) Filed: Feb. 21, 2006

(51) Int. Cl.
A61M 16/00 (2006.01)
(52) U.S. Cl. .............. 128/204.18; 363/44; 363/125
(58) Field of Classification Search ........ 318/720–724; 320/135, 136; 323/229, 311, 349; 363/34–48, 363/123, 125, 129, 50–53, 73; 128/204.18, 128/204.21
See application file for complete search history.

(56) References Cited

U.S. PATENT DOCUMENTS

| | | | |
|---|---|---|---|
| 4,969,885 A * | 11/1990 | Farin | 606/38 |
| 5,009,225 A * | 4/1991 | Vrabel | 128/201.24 |
| 5,477,091 A * | 12/1995 | Fiorina et al. | 307/66 |
| 5,797,852 A | 8/1998 | Karakasoglu et al. | |
| 6,057,609 A * | 5/2000 | Nagai et al. | 307/66 |
| 6,225,708 B1 * | 5/2001 | Furukawa et al. | 307/66 |
| 6,281,485 B1 * | 8/2001 | Siri | 250/203.4 |
| 6,329,796 B1 | 12/2001 | Popescu | |
| 6,392,555 B1 | 5/2002 | Most, Jr. | |
| 6,404,168 B1 | 6/2002 | Shoji | |
| 6,414,403 B2 * | 7/2002 | Kitagawa et al. | 307/66 |
| 6,762,842 B2 * | 7/2004 | Pfeifer et al. | 356/436 |
| 6,912,123 B2 | 6/2005 | Sakai et al. | |
| 6,988,498 B2 * | 1/2006 | Berthon-Jones et al. | 128/204.23 |
| 2005/0099750 A1 | 5/2005 | Takahashi et al. | |
| 2005/0156568 A1 | 7/2005 | Yuch | |
| 2005/0182991 A1 | 8/2005 | Kawakubo | |
| 2005/0240814 A1 | 10/2005 | Sasakura et al. | |

FOREIGN PATENT DOCUMENTS

JP      408185893 A      7/1996

* cited by examiner

Primary Examiner—Bentsu Ro
(74) Attorney, Agent, or Firm—Hoglund & Pamias PSC; Roberto J. Rios

(57) ABSTRACT

An uninterruptible D.C. battery backup power supply is designed to operate medical respiratory treatment equipment such as a machine for the treatment of sleep apnea. A power supply with D.C. backup consists of a rectifier/charger, a rechargeable battery and a D.C.-to-D.C. converter. The rectifier/charger is connected to the wall outlet providing the D.C. charging capacity as well as the capacity to provide power to the D.C.-to-D.C. converter which provides D.C. power to the equipment being protected during a momentary interruption in the A.C. commercial voltage or a prolonged power outage.

19 Claims, 4 Drawing Sheets

METHODS OF POWERING MEDICAL EQUIPMENT FOR THE TREATMENT OF SLEEP APNEA

FIELD OF THE INVENTION

The present invention relates generally to the operation of machines used for the treatment of sleep apnea. More particularly, the invention relates to providing back-up power to such machines upon a failure of a commercial power grid.

BACKGROUND

Sleep apnea is a common sleeping disorder characterized by a brief interruption of breathing during a sleeping period. These episodes can last up to 10 seconds and occur repeatedly throughout the sleeping period. People with sleep apnea will partially awaken as they struggle to breathe and in the morning they will not be aware of the disturbance in their sleep. This condition affects over 12 million people. Not treating this condition may result in high blood pressure and a decrease in hemoglobin oxygen level. Untreated cases of sleep apnea can cause a person to fall asleep during normal activities such as working at a computer, talking on the phone or driving a car (which can be fatal).

There are three types of sleep apnea: (1) Obstructive Sleep Apnea (OSA), which is the most common, caused by relaxation of the soft tissue in the back of the throat that blocks the air passage; (2) Central Sleep Apnea (CSA) caused by irregularities in the brain's normal signals to breathe; and (3) Mixed Sleep Apnea (MSA), which is a combination of these two.

One of the methods applied to treat sleep apnea is to use a continuous positive airway pressure (C-Pap) machine or a bi-level positive airway pressure (Bi-Pap) machine. This equipment consists of a face mask which covers the nose and/or mouth area. The face mask is attached to a tube and a motor with a compressor that blows pressurized air into the mask and through the patient's airway to keep it open. This machine is designed to assure that the patient is able to experience a deep and adequate sleeping period. During the use of the C-Pap machine, when the A.C. power source is interrupted for a few seconds, the unit goes into a fault alarm that causes the machine to stop providing pressurized air flow. Because airflow has stopped and the patient's air passage is covered with a face mask, this has the unfortunate consequence of suffocating the patient while he or she is asleep. When there is a prolonged A.C. power outage the machine simply turns off and the same result is obtained where a suffocating period commences.

Present day solutions to this problem suggest a rechargeable battery connected to the machine by means of a D.C. connector. The respiratory machine is sensitive to the D.C. voltage it uses and its stability. Commonly the input voltage range is 11-14 volts D.C. Once the battery is depleted the user must then recharge the rechargeable battery with a battery charger. The most common problem is not charging the battery when required, which deteriorates the capacity to store energy. When the battery is over-charged the battery can spill acid and fumes that may cause serious damage to skin, eyes or irritation of the respiratory passage. The charging procedure requires that the D.C. adaptor cable which is connected to the machine be removed while recharging the battery. This avoids high voltage and current to be exposed to the machine during the charging cycle, which may cause damage. However the patient must take caution in not shorting out the D.C. connection cable with the battery terminals which are exposed. A patient must also take caution that no metal objects short out the battery terminals damaging the battery as well as causing danger to the patient due to spark and acid contents. Patient must store the charger and place the battery in a dry safe area and periodically recharge the battery to maintain its capacity to store energy.

One obvious problem with this configuration is the maintenance required to maintain the battery. Another less obvious problem results from the operation of the C-Pap machine. Specifically, upon a momentary loss of power, the C-Pap machine may activate an alarm to alert the patient of the condition. One example of such a system is shown in U.S. Pat. No. 6,392,555, titled "Medical Equipment Warning Device," which issued to Most, Jr., on May 21, 2002. It is important that patients being treated for sleep apnea should not be awoken unless absolutely necessary. Waking such a patient upon a momentary lapse of power is counterproductive to treatment.

Hospitals generally have auxiliary power sources that supply electricity if the primary source fails for any reason. Hospital auxiliary power is provided within seconds when there is a power failure. Individual homes generally do not have an auxiliary power source unless it is a backup generator. In the unlikely event of a power failure in a hospital, home care facility or a residence there is an interruption of power to the machine. If an immediate manual reset is not performed the machine will stop operating and the patient will experience a suffocating episode. Once the auxiliary power source is supplying power, it is necessary to manually reset the respiratory machine. A person that depends on a respiratory machine to treat sleep apnea requires a backup device that will assure that his sleep is not interrupted due to a power failure or alarm.

SUMMARY OF THE INVENTION

One object of the invention is to provide an uninterruptible backup D.C. power supply producing hours of power to a respiratory medical machine as well as non-medical devices when commercial power is interrupted, fails or is not available.

Another object of the invention is to connect external batteries so as to provide a specific critical minimum of backup time required.

Another object of the invention is to avoid waking the patient merely upon a loss of A.C. power but only to wake a patient when needed to prevent an immanent suffocation event that would occur upon the exhaustion of battery back-up.

According to one aspect of the invention, the backup power supply connects through a D.C. connector so that it can also be used wherever an auxiliary D.C. power source may be required for other medical or non-medical equipment such as security panels, communications equipment, computer peripherals and remote sites where no commercial power is available.

According to another aspect of the invention, a machine for the treatment of sleep apnea such as a C-Pap machine is operated on D.C. power. The machine includes a motor and compressor that are operationally coupled with a mask for delivering pressurized air to a patient. A power supply system provides D.C. power to the sleep apnea machine. The power supply system includes an A.C.-to-D.C. converter, a rechargeable battery and a D.C.-to-D.C. converter. The A.C.-to-D.C. converter receives an A.C. power input and converts the A.C. power into a D.C. power output. The rechargeable battery is operationally coupled with the D.C. power output of the A.C.-to-D.C. converter. The D.C.-to-D.C. converter is operationally coupled with the rechargeable battery and the D.C. power output of the A.C.-to-D.C. converter. The D.C.-to-D.C. converter receives a D.C. voltage within a range having a minimum and a maximum and outputs a D.C. voltage at a fixed level for powering the machine for the treatment of sleep apnea. An audible alarm sufficient to wake a sleeping patient is activated when the rechargeable battery is nearly depleted (below 9.8 volts) and A.C. power to the A.C.-to-D.C. converter fails. The audible alarm, however, is not activated when the rechargeable battery is able to provide power sufficient to operate the machine for the treatment of sleep apnea.

According to further aspects of the invention, a power-failure indicator is operationally coupled with the A.C. power input and activates a visual indicator upon loss of A.C. power. The visual indicator remains activated after restoration of A.C. power and is deactivated only by a manual reset. The visual indicator is a LED that does not wake a patient upon activation. The power supply system is housed within a single enclosure and includes a fan.

According to still further aspects of the invention, the A.C.-to-D.C. converter is a constant current switch-mode battery charger suitable for converting 120 volts A.C. to 12 volts D.C. The rechargeable battery is a 12 volt D.C. battery. The D.C.-to-D.C. converter is capable of receiving a D.C. voltage from as low as 9.2 volts to as high as 15 volts and providing the fixed level for powering the machine for the treatment of sleep apnea at an output of 12 volts +/−1%. It provides over voltage and overload protection.

According to another aspect of the invention, a machine for the treatment of sleep apnea is especially suited for distinguishing between a short interruption of A.C. power, which does not require alerting a sleeping patient, and a prolonged interruption of A.C. power, which may require alerting a sleeping patient. To this end, an A.C.-to-D.C. converter converts A.C. input power to D.C. A rechargeable battery is operationally coupled with the A.C.-to-D.C. converter. A D.C.-to-D.C. converter is operationally coupled with the A.C.-to-D.C. converter and the rechargeable battery. The D.C.-to-D.C. converter receives a D.C. voltage within a range having a minimum and a maximum. The range extends over at least two volts and provides an output D.C. voltage at a fixed level. The machine is powered by a D.C. voltage and is operationally coupled with the D.C.-to-D.C. converter. When the A.C.-to-D.C. converter receives A.C. input power, the machine is powered through the D.C.-to-D.C. converter by the A.C.-to-D.C. converter. When the A.C.-to-D.C. converter does not receive A.C. input power the machine is powered through the D.C.-to-D.C. converter by the rechargeable battery. An audible alarm sufficient to wake a patient from sleep is activated when an output voltage from the rechargeable battery is approximately at or near the minimum of the range of the D.C.-to-D.C. converter and the A.C.-to-D.C. converter is not receiving A.C. input power but not when the output voltage from the rechargeable battery is substantially above the minimum range of the D.C.-to-D.C. converter and the A.C.-to-D.C. converter is not receiving A.C. input power. According to further aspects of the invention, the A.C.-to-D.C. receives an input anywhere between 96-267 volts at 47-63 Hz and converts this to a nominal 12 volts D.C. A latched visual indicator is activated upon a loss of A.C. power to the A.C.-to-D.C. converter. The latched visual indicator is insufficient to wake a sleeping patient. The latched visual indicator remains active after resumption of A.C. power to the A.C.-to-D.C. converter until a patient manually resets the latched visual indicator.

DETAILED DESCRIPTION

According to one aspect of the invention, C-Pap machines for the treatment of sleep apnea are powered by A. C. and can be powered by D.C. electricity. Input A.C. power is rectified and converted to charge a battery. The output from this battery passes through a D.C.-to-D.C. converter to power the machine. The D.C.-to-D.C. converter operates so that even when the output voltage of the battery drops below the C-PAP DC threshold, the output of the converter maintains the voltage to continue providing a sufficient level to power the machine. The output level of the D.C.-to-D.C. converter is selected to match the input voltage requirement of the machine. Upon a temporary loss of A.C. power, the patient is not woken up because no audible alarm is activated and the interruption of A.C. power does not interrupt the flow of power from the battery. Thus, the machine will continue to function normally until the battery is depleted or discharged. The D.C.-to-D.C. converter also operates to isolate power spikes or surges from the A.C. power grid or from the process of charging the battery.

Figure 1:
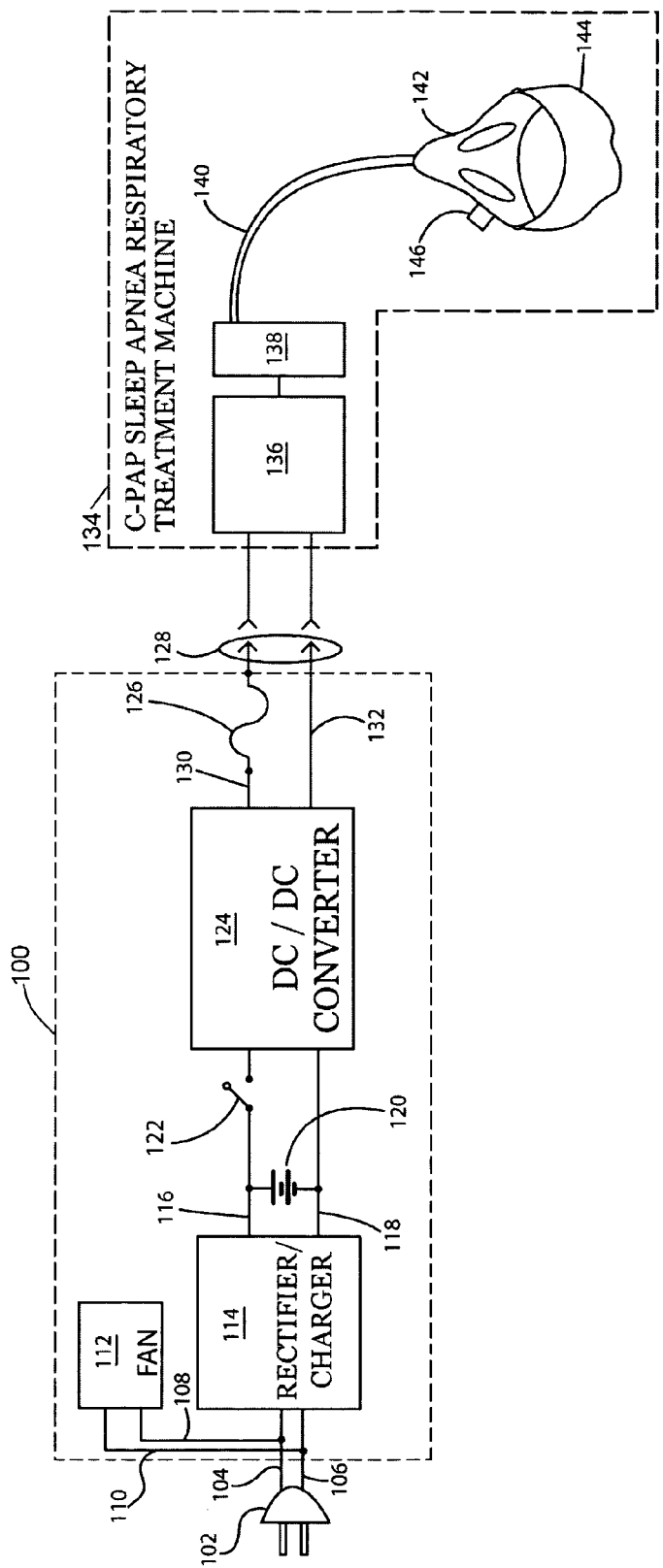
FIG. 1 is a functional block diagram of a circuit, with an internal battery, used to power a machine for the treatment of sleep apnea.

Turning to FIG. 1, a continuous positive air pressure (C-Pap) sleep apnea respiratory treatment machine 134 with an uninterruptible D.C. power source 100 is shown. Although shown as a C-Pap machine, any other medical or non-medical equipment operable on D.C. power could be substituted. The uninterruptible D.C. power source 100 includes an A.C. power plug 102, a cooling fan 112, a rectifier/charger 114, a rechargeable battery 120, a manual operating switch 122, a D.C.-to-D.C. converter 124, output line fuse 126 and a D.C. plug 128. The C-Pap machine 134 consists of a D.C. motor 136, a compressor 138, an air supply tube 140, a plastic mask 142 with an elastic band 144 and an air discharge opening 146.

In one preferred implementation, the rectifier/charger 114 is available from Soniel International Limited. It is a 12 volt DC Battery Charger, Model 1206S. The D.C.-to-D.C. converter 124 is available from Mean Well USA, Inc. It is a 12 volt DC converter, Model SD-50A-12. The rechargeable battery 120 is available from Enersis, Inc. It is a 12 volt DC Battery, model NP-GEL30-12.

The rectifier/charger 114 is energized by an A.C. source to the A.C. power plug 102 by lines 104 and 106. The A.C. source voltage energizes the cooling fan 112 by lines 108 and 110. The cooling fan 112 maintains an ambient operating temperature for adequate operation. The rectifier/charger 114 supplies the D.C. charging current to the rechargeable battery 120 by lines 116 and 118.

The manual operating switch 122 connects the D.C. voltage to the D.C.-to-D.C. converter 124. The D.C.-to-D.C. converter 124 supplies stable, clean and uninterrupted D.C. voltage to the C-Pap machine 134 by lines 130 and 132. This circuit is protected with an in-line fuse 126 connected to the D.C. plug 128. The C-Pap machine 134 consist of a D.C. electric motor 136 and a compressor 138. The compressor 138 supplies air under pressure through a supply tube 140. An elastic band 144 holds the plastic mask 142 over a patient's nose and/or mouth area. An air discharge valve 146 is attached to the mask 142. The specific configuration of the air discharge valve 146 depends on the type of mask used for discharging air from the lungs of a patient wearing the mask 142 during expiration.

With the manual operating switch 122 closed, an interruption in the A.C. source to the power plug 102 will cause the rectifier/charger 114 and the fan 112 to turn off. The rechargeable battery 120 by lines 116 and 118 supplies the D.C. voltage to the D.C.-to-D.C. converter 124. The D.C.-to-D.C. converter 124 supplies clean, uninterrupted, stable and isolated D.C. voltage to the C-Pap machine 134.

Once the A.C. source is restored to the power plug 102 the cooling fan 112 will start circulating air and the rectifier/charger 114 will commence the charging cycle to the rechargeable battery 120 by lines 116 and 118. This operational process is performed automatically and without the assistance of the patient. The C-Pap machine 134 is powered only by the uninterruptible D.C. power supply. Upon an extended power outage, the patient my wake up due to discomfort because of a noticeable change in room temperature but should not experience a suffocating episode. In the event that power is lost and the patient remains sleeping for a period of time sufficient to exhaust the battery, the patient can be woken by a separate alarm circuit or the C-Pap machine itself. Specifically, the C-Pap machine 134 can include an audible wake-up alarm powered by a small D.C. battery. Alternatively, a separate circuit can be used to detect when the output of the battery 120 or the D.C.-to-D.C. converter falls below a predetermined level. This would activate an audible alarm. One suitable circuit is described further below with reference to FIG. 4.

Figure 2:
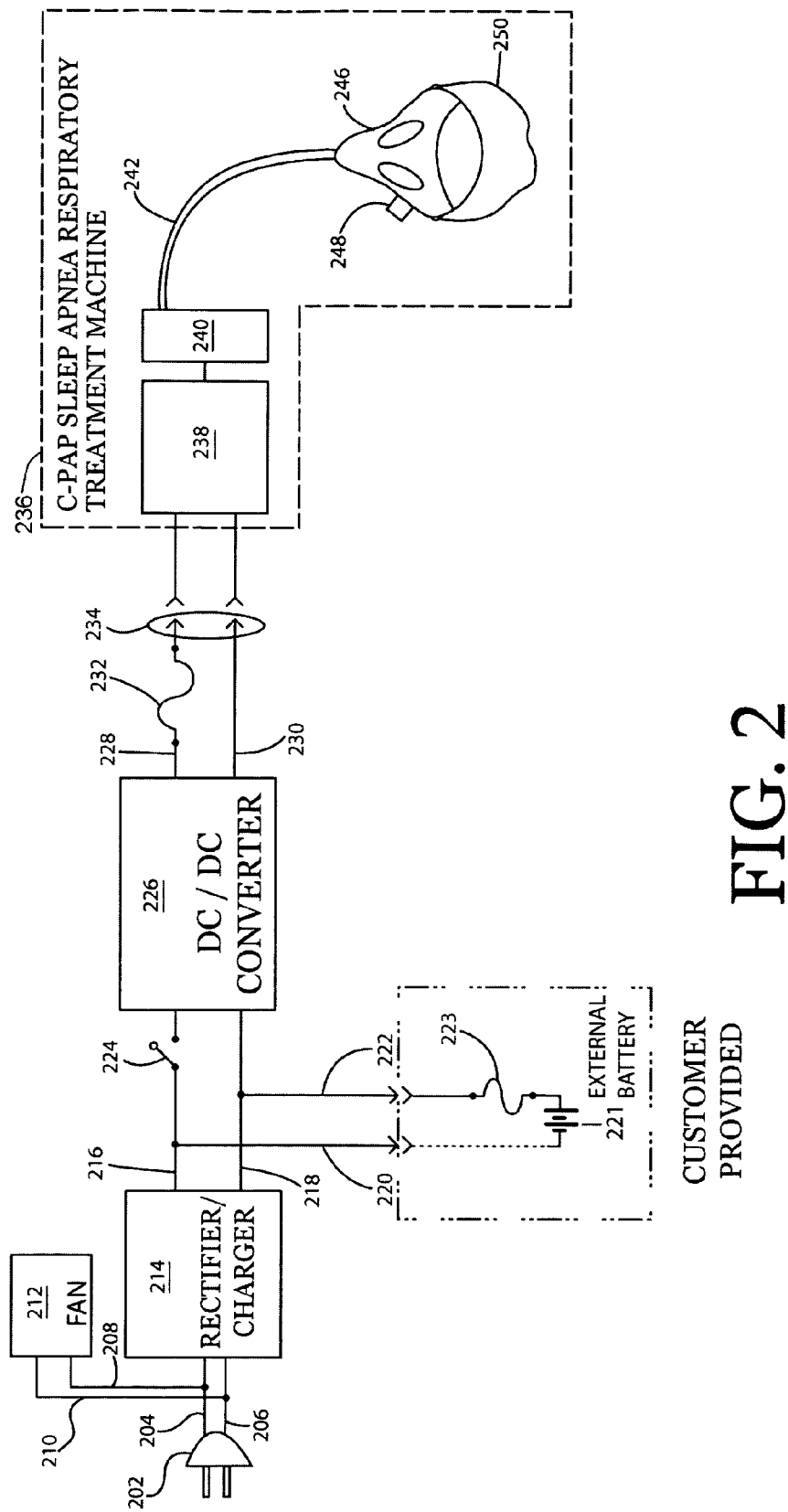
FIG. 2 is a functional block diagram of another circuit, with an external battery, used to power a machine for the treatment of sleep apnea.

Turning to FIG. 2, another C-Pap machine 236 with an uninterruptible D.C. power source is shown. This circuit uses an external battery 221. More specifically, the uninterruptible D.C. power source includes an A.C. power plug 202, a cooling fan 212, a rectifier/charger 214, an external rechargeable battery 221 with external D.C. fuse 223, a manual operating switch 224, a D.C.-to-D.C. converter 226, output in-line fuse 232 and a D.C. plug 234. The rectifier/charger 214, the fan 212 and the D.C.-to-D.C. converter 226 are housed in a common enclosure. The C-Pap machine 236 consist, of a D.C. motor 238, a compressor 240, an air supply tube 242, a plastic mask 246 with an elastic band 250 and an air discharge valve 248.

The rectifier/charger 214 is energized by an A.C. source to the A.C. power plug 202 by lines 204 and 206. The A.C. source voltage energizes the cooling fan 212 by lines 208 and 210. The cooling fan 212 maintains an ambient operating temperature for adequate operation. The rectifier/charger 214 supplies the D.C. charging current to the external rechargeable battery 221 by lines 220 and 222 from lines 216 and 218.

The manual operating switch 224 connects the D.C. voltage to the D.C.-to-D.C. converter 226 by lines 216 and 218. The D.C.-to-D.C. converter 226 supplies stable, clean and uninterrupted D.C. voltage to the C-Pap machine 236 by lines 228 and 230. Line 228 has an in-line fuse 232 which is connected to a D.C. plug 234.

With the manual operating switch 224 closed, an interruption in the A.C. power source connected to the A.C. power plug 202 will cause the rectifier/charger 214 and the fan 212 to turn off. The external rechargeable battery 221 supplies the D.C. voltage to the D.C.-to-D.C. converter 226 through lines 220 and 222. The D.C.-to-D.C. converter 226 supplies clean, uninterrupted, stable and isolated D.C. voltage to the C-Pap machine 236. Once the A.C. power source is restored to the power plug 202, the cooling fan will start circulating air and the rectifier/charger 214 will commence the charging cycle to the external rechargeable battery 221 by lines 220 and 222 from lines 216 and 218.

Preferably, C-Pap machine 236 includes an audible alarm that is activated upon loss of power. In the event that the external battery 221 is fully depleted, the C-Pap machine 236 will activate its audible alarm so that the patient is woken by this rather than by suffocation caused by loss of airflow to the mask 246.

Figure 3:
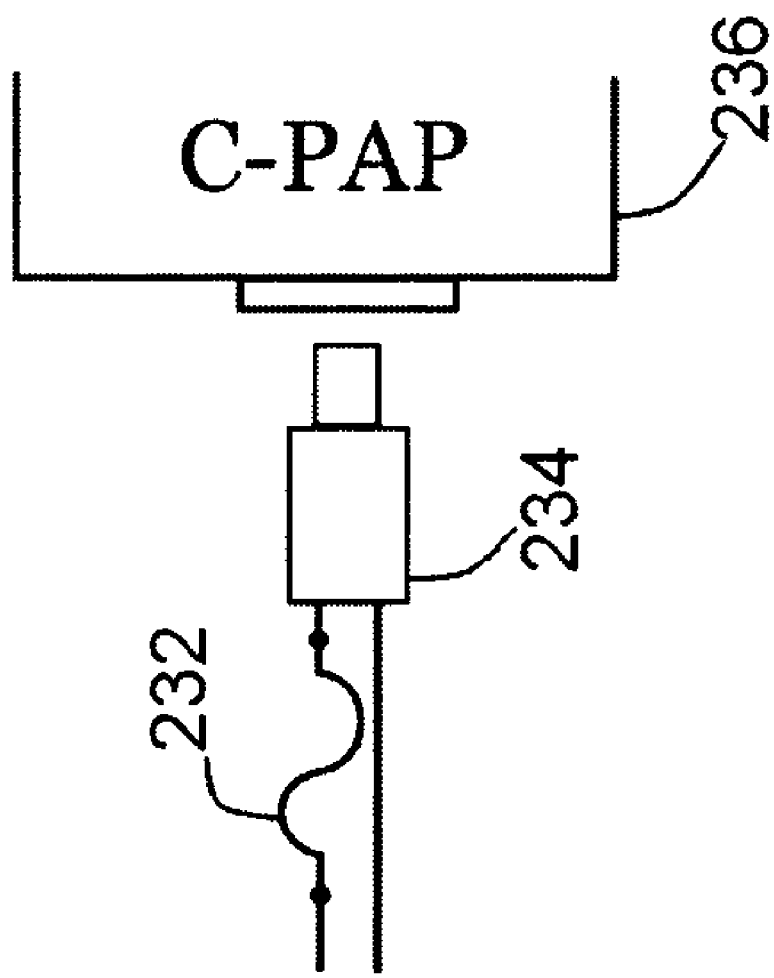
FIG. 3 is a block diagram showing the D.C. plug used to connect the circuit to the machine for the treatment of sleep apnea in FIG. 2.

Turning to FIG. 3, the connection between the uninterruptible power source and the C-Pap machine is shown in further detail. The D.C. plug 234 is a standard tubular connection. It has one connection that extends from its center axis and another tubular connection that is concentric with the center axis. One preferred plug is commercially available from Memory Protection Devices, Inc., Model No. 172-4000.

Figure 4:
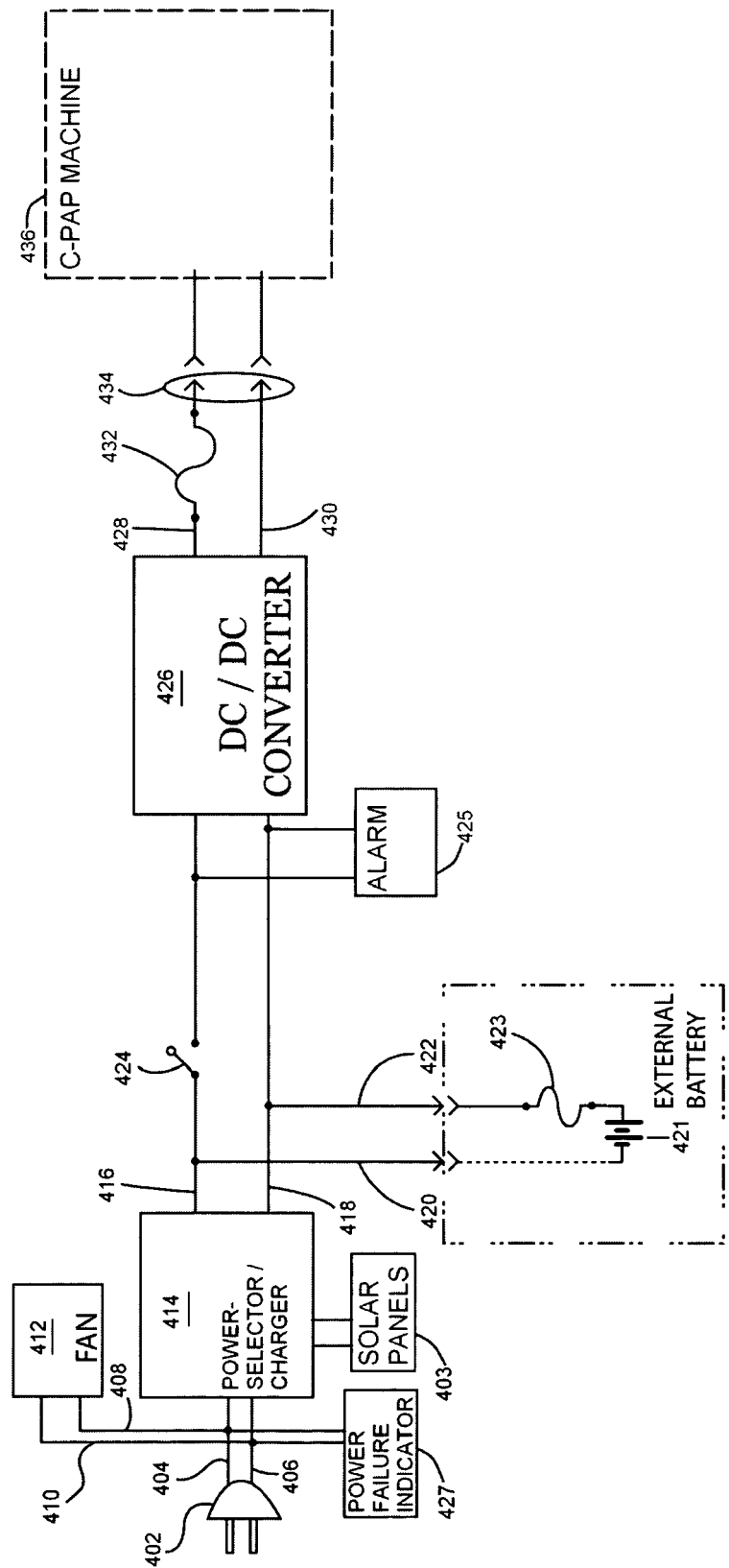
FIG. 4 is a functional block diagram of another circuit used to power a machine for the treatment of sleep apnea.

Turning to FIG. 4, another C-Pap machine 436 with an uninterruptible D.C. power source is shown. This circuit uses an external battery 421, which is recharged either by A.C. power or solar panels 403. More specifically, the uninterruptible D.C. power source includes an A.C. power plug 402, a cooling fan 412, a set of solar panels 403, a power-selector/charger 414, an external rechargeable battery 421 with external D.C. fuse 423, a manual operating switch 424, an alarm 425, D.C.-to-D.C. converter 426, a power-failure indicator 427, output in-line fuse 432 and a D.C. plug 434. The power-selector/charger 414, the fan 412, the alarm 425, the D.C.-to-D.C. converter 426 and the power-failure indicator 427 are housed in a common enclosure.

The power-selector/charger 414 is energized by an A.C. source to the A.C. power plug 402 by lines 404 and 406. Preferably this is an electronic selector but can be manual. Alternatively, during daylight hours, the charger 414 is powered by solar panels 403. The power-selector/charger 414 makes the selection between these two sources. When powered by A.C., the A.C. source voltage energizes the cooling fan 412 by lines 408 and 410. The cooling fan 412 maintains an ambient operating temperature for adequate operation. The power-selector/charger 414 supplies the D.C. charging current to the external rechargeable battery 421 by lines 420 and 422 from lines 416 and 418.

The manual operating switch 424 connects the D.C. voltage to the D.C.-to-D.C. converter 426 by lines 416 and 418. The D.C.-to-D.C. converter 426 supplies stable, clean and uninterrupted D.C. voltage to the C-Pap machine 436 by lines 428 and 430. Line 428 has an in-line fuse 432 which is connected to a D.C. plug 434.

With the manual operating switch 424 closed, and while running on A.C. power, an interruption in the A.C. power source connected to the A.C. power plug 402 will cause the fan 412 to turn off. The external rechargeable battery 421 supplies the D.C. voltage to the D.C.-to-D.C. converter 426 through lines 420 and 422. The D.C.-to-D.C. converter 426 supplies clean, uninterrupted, stable and isolated D.C. voltage to the C-Pap machine. Once the A.C. power source is restored to the power plug 402 and during non-daylight hours, the cooling fan will start circulating air and the power-selector/charger 414 will commence the charging cycle to the external rechargeable battery 421 by lines 420 and 422 from lines 416 and 418.

Preferably, this system includes an audible alarm that is activated prior to a complete loss of power, including battery power. Specifically, when the A.C. power fails and it is night so that there is no power from the solar panels 403, the C-Pap machine 436 will run on battery power. Ordinarily, the battery is sufficient to power the C-Pap machine for at least an eight hour period so that a patient would be able to complete a night's rest without being woken due to a power failure. If, however, the patient continued sleeping for a substantially longer period, the battery 421 may become depleted. Alarm 425 monitors the power level of the battery 421. It should ordinarily provide 12 VD.C., but will drop below this level as it becomes depleted. The D.C.-to-D.C. converter 426 supplies clean, stable and isolated D.C. voltage as the battery voltage drops below this level. However, a continued drop in the output voltage level of battery 421 indicates that it is running out of power. Alarm 425 monitors the output voltage level of battery 421. If this drops below a predetermined level, for example 9.5 volts, it activates an audible alarm. This alarm is intended to wake the patient before a complete power failure so that the patient does not suffer a suffocating episode when the C-Pap machine 436 stops providing pressurized air. The specific level for this alarm should be selected based upon the specific characteristics of the battery that is used. It should be selected to provide sufficient time for the audible alarm to wake the patient before a loss of power to the C-Pap machine 436 that would cause a suffocating experience.

The separate power-failure indicator 427 is used to alert a patient that there was a power failure during the evening. In normal operation, if the A.C. power fails during the evening for a limited period of time, the C-Pap machine 436 will run on the battery 421 provided switch 424 is closed. If power is restored before exhausting that energy supply, the patient may complete his or her rest without being alerted as to the power failure. To provide an indication of such failure to the patient, the circuit includes the power-failure indicator 427. This circuit has a relay with a manual reset and an LED indicator. If power is lost, the relay activates the LED indicator, which is powered by a separate battery. This remains activated after power is restored. The power-failure indicator 427 must be manually reset by the patient.

This power-failure indicator 427 provides useful information to the patient for a number of reasons. First, after a power failure, the battery 421 should be given sufficient time to fully recharge before the next operation. This insures that in the event of another power failure, the battery 421 will have sufficient power to sustain operation of the C-Pap machine 436 through the night. Second, although the C-Pap machine 436 will continue to operate on battery backup power during a power failure, other systems such as heating or air conditioning may fail. This may diminish the patients ability to obtain complete rest and the patient may wake up without feeling fully refreshed. Absent a power-failure indicator, the patient may believe that there is a problem with the C-Pap machine 436 that is inhibiting his or her rest. The power-failure indicator 427 alerts the patient as to the other potential causes.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

I claim:

1. A method of operating a machine for the treatment of sleep apnea comprising:
   providing a machine for the treatment of sleep apnea that operates on D.C. power, wherein the machine includes a motor and compressor that are operationally coupled with a mask for delivering pressurized air to a patient;
   providing a power supply system for providing D.C. power to the sleep apnea machine, wherein the power supply system includes:
      an A.C.-to-D.C. converter for receiving an A.C. power input and converting the A.C. power into a D.C. power output;
      a rechargeable battery operationally coupled with the D.C. power output of the A.C.-to-D.C. converter; and
      a D.C.-to-D.C. converter operationally coupled with the rechargeable battery and the D.C. power output of the A.C.-to-D.C. converter, wherein the D.C.-to-D.C. converter receives a D.C. voltage within a range having a minimum and a maximum and outputs a D.C. voltage at a fixed level for powering the machine for the treatment of sleep apnea; and
   activating an audible alarm sufficient to wake a sleeping patient when the rechargeable battery is nearly depleted and A.C. power to the A.C.-to-D.C. converter fails but not activating the audible alarm when the rechargeable battery is able to provide power sufficient to operate the machine for the treatment of sleep apnea.

2. The method of claim 1, further comprising the step of providing a power-failure indicator, wherein the power failure-indicator is operationally coupled with the A.C. power input and activates a visual indicator upon loss of A.C. power, wherein the visual indicator remains activated after restoration of A.C. power and is deactivated only by a manual reset and wherein the visual indicator does not wake a patient upon activation.

3. The method of claim 2, wherein the visual indicator comprises a LED.

4. The method of claim 1, wherein the step of providing the machine for the treatment of sleep apnea comprises providing a continuous positive airway pressure machine.

5. The method of claim 1, wherein the step of providing the power supply system comprises providing a single enclosure that houses the A.C.-to-D.C. converter, the rechargeable battery and the D.C.-to-D.C. converter.

6. The method of claim 5, wherein the method further comprises providing a fan positioned within the single enclosure and powered by the A.C. power input.

7. The method of claim 1, wherein in the step of providing the A.C.-to-D.C. converter, the rechargeable battery and the D.C.-to-D.C. converter, the A.C.-to-D.C. converter is suitable for converting 120 volts A.C. to 12 volts D.C., the rechargeable battery is a 12 volt D.C. battery, and the D.C.-to-D.C. converter is capable of receiving a D.C. voltage from as low as 9.2 volts to as high as 15 volts and providing the fixed level for powering the machine for the treatment of sleep apnea at an output of 12 volts +/−1%.

8. The method of claim 7, wherein the step of activating the audible alarm comprises activating the audible alarm when an output voltage of the rechargeable battery falls below a threshold of 9.8 volts.

9. The method of claim 1, further comprising the step of providing a solar panel operationally coupled with the rechargeable battery to provide power to the rechargeable battery during daylight hours.

10. The method of claim 1, wherein the step of providing the A.C.-to-D.C. converter comprises providing a constant current switch-mode battery charger.

11. The method of claim 1, wherein the step of providing the D.C.-to-D.C. converter comprises providing over voltage and overload protection.

12. A method of operating a machine for the treatment of sleep apnea and especially suited for distinguishing between a short interruption of A.C. power, which does not require alerting a sleeping patient, and a prolonged interruption of A.C. power, which may require alerting a sleeping patient, comprising the steps of:
providing an A.C.-to-D.C. converter for converting A.C. input power to D.C.;
providing a rechargeable battery operationally coupled with the A.C.-to-D.C. converter;
providing a D.C.-to-D.C. converter operationally coupled with the A.C.-to-D.C. converter and the rechargeable battery, wherein the D.C.-to-D.C. converter receives a D.C. voltage within a range having a minimum and a maximum and wherein the range extends over at least two volts and provides an output D.C. voltage at a fixed level;
providing a machine for the treatment of sleep apnea, wherein the machine is powered by a D.C. voltage and is operationally coupled with the D.C.-to-D.C. converter, wherein when the A.C.-to-D.C. converter receives A.C. input power the machine is powered through the D.C.-to-D.C. converter by the A.C.-to-D.C. converter and wherein when the A.C.-to-D.C. converter does not receive A.C. input power the machine is powered through the D.C.-to-D.C. converter by the rechargeable battery; and activating an audible alarm sufficient to wake a patient from sleep when an output voltage from the rechargeable battery is approximately at or near the minimum of the range of the D.C.-to-D.C. converter and the A.C.-to-D.C. converter is not receiving A.C. input power but not when the output voltage from the rechargeable battery is substantially above the minimum range of the D.C.-to-D.C. converter and the A.C.-to-D.C. converter is not receiving A.C. input power.

13. The method of claim 12, wherein the step of providing the A.C.-to-D.C. converter comprises accepting an A.C. voltage ranging from 96-267 volts at 47-63 Hz and converting the A.C. voltage to a nominal 12 volts D.C.

14. The method of claim 12, wherein the step of providing the machine for the treatment of sleep apnea comprises providing a continuous positive airway pressure machine.

15. The method of claim 12, further comprising the step of activating a latched visual indicator upon a loss of A.C. power to the A.C.-to-D.C. converter, wherein the latched visual indicator is insufficient to wake a sleeping patient and wherein the latched visual indicator remains active after resumption of A.C. power to the A.C.-to-D.C. converter until a patient manually resets the latched visual indicator.

16. The method of claim 12, further comprising the step of providing a fan operationally coupled with the A.C. input power.

17. The method of claim 12, further comprising the step of providing a fuse operationally coupled between the D.C.-to-D.C. converter and the machine for the treatment of sleep apnea.

18. The method of claim 12, further comprising the step of providing a fuse operationally coupled between the external rechargeable battery and the A.C.-to-D.C. converter.

19. The method of claim 12, further comprising the step of providing a detachable connector between the D.C.-to-D.C. converter and the machine for the treatment of sleep apnea.

* * * * *